US012589201B2

(12) United States Patent
Loudermilk et al.

(10) Patent No.: US 12,589,201 B2
(45) Date of Patent: Mar. 31, 2026

(54) METHOD AND SYSTEM FOR PROVIDING A THERAPEUTIC AGENT TO AN IMPLANTED INFUSION DEVICE

(71) Applicant: B. Braun Miethke GmbH & Co. KG, Potsdam (DE)

(72) Inventors: Brandon Loudermilk, Potsdam (DE); Michael Sörensen, Potsdam (DE)

(73) Assignee: B. Braun Miethke GmbH & Co. KG, Potsdam (DE)

( * ) Notice: Subject to any disclaimer, the term of this patent is extended or adjusted under 35 U.S.C. 154(b) by 54 days.

(21) Appl. No.: 18/328,866

(22) Filed: Jun. 5, 2023

(65) Prior Publication Data

US 2024/0399057 A1 Dec. 5, 2024

Related U.S. Application Data

(62) Division of application No. 16/799,864, filed on Feb. 25, 2020, now Pat. No. 11,707,568.

(Continued)

(51) Int. Cl.
A61M 5/158 (2006.01)
A61M 5/142 (2006.01)
(Continued)

(52) U.S. Cl.
CPC ...... A61M 5/14276 (2013.01); A61M 5/1582 (2013.01); A61M 5/162 (2013.01);
(Continued)

(58) Field of Classification Search
CPC .. A61M 2039/0217; A61M 2039/0211; A61M 2039/0244; A61M 2205/0244;
(Continued)

(56) References Cited

U.S. PATENT DOCUMENTS 3,552,441 A * 1/1971 Luhleich ............... F16K 11/065
138/155
4,222,374 A * 9/1980 Sampson .......... A61M 39/0208
623/66.1

(Continued)

FOREIGN PATENT DOCUMENTS

CN 107921202 A 4/2018
CN 108136102 A 6/2018
WO 2013052414 A2 4/2013

OTHER PUBLICATIONS

China National Intellectual Property Administration, Office Action in related application CN20208017361.

(Continued)

*Primary Examiner* — Quynh-Nhu H. Vu
(74) *Attorney, Agent, or Firm* — Smartpat PLC

(57) ABSTRACT

A system for refilling a multi-chamber implantable infusion device is presented. The infusion device has a refill chamber which is accessible through an external septum of a refill port. The refill chamber is divided by an inner septum into an upper reservoir and a lower reservoir. The lower refill chamber is refilled with lower reservoir needles having a needle opening axially placed to align with the lower reservoir. The upper reservoir is refilled with an upper reservoir needle having an opening aligned with the upper reservoir. Magnetic portions are provided in the needles to localize and identify the needle. A processor within the infusion device is connected to magnetic field sensors which sense magnetic portions of the needle and recognize information encoded magnetically within the needle.

6 Claims, 6 Drawing Sheets

Related U.S. Application Data

(60) Provisional application No. 62/811,161, filed on Feb. 27, 2019.

(51) Int. Cl.
*A61M 5/162* (2006.01)
*A61M 5/168* (2006.01)

(52) U.S. Cl.
CPC . *A61M 5/16809* (2013.01); *A61M 2005/1588* (2013.01); *A61M 2205/0244* (2013.01); *A61M 2205/14* (2013.01); *A61M 2205/3317* (2013.01); *A61M 2205/3523* (2013.01); *A61M 2205/50* (2013.01); *A61M 2205/502* (2013.01); *A61M 2205/52* (2013.01); *A61M 2209/045* (2013.01)

(58) Field of Classification Search
CPC ...... A61M 2205/14; A61M 2205/3317; A61M 2209/045; A61M 39/0208; A61M 5/14276; A61M 5/1582; A61M 5/162; A61M 5/16809; A61M 5/329; A61M 5/3291
See application file for complete search history.

(56) References Cited

U.S. PATENT DOCUMENTS

| | | | | |
|---|---|---|---|---|
| 4,571,749 | A * | 2/1986 | Fischell | A61F 2/004 600/561 |
| 4,573,994 | A | 3/1986 | Fischell et al. | |
| 4,784,646 | A * | 11/1988 | Feingold | A61M 39/0208 604/9 |
| 4,804,054 | A | 2/1989 | Howson et al. | |
| 5,431,640 | A * | 7/1995 | Gabriel | A61J 15/0007 600/12 |
| 6,520,936 | B1 * | 2/2003 | Mann | A61M 5/14276 604/141 |
| 6,962,580 | B2 * | 11/2005 | Adams | A61M 39/0208 604/288.02 |
| 7,338,028 | B2 * | 3/2008 | Zimmerling | A61M 39/22 251/7 |
| 7,399,445 | B2 | 7/2008 | Kuroda et al. | |
| 7,637,897 | B2 * | 12/2009 | Ginggen | A61M 5/14276 604/288.01 |
| 7,744,589 | B2 * | 6/2010 | Mounce | A61M 5/1413 604/890.1 |
| 8,171,938 | B2 * | 5/2012 | Bengtson | A61M 39/0208 128/899 |
| 8,208,146 | B2 | 6/2012 | Srinivasan et al. | |
| 8,221,439 | B2 * | 7/2012 | Dlugos, Jr. | A61F 5/0059 606/151 |
| 8,784,389 | B2 | 7/2014 | Stern et al. | |
| 9,603,997 | B2 | 3/2017 | Humayun et al. | |
| 10,471,206 | B2 * | 11/2019 | Dittrich | A61J 1/2013 |
| 11,052,185 | B2 | 7/2021 | Larsen et al. | |
| 2004/0073196 | A1 | 4/2004 | Adams et al. | |
| 2004/0256584 | A1 * | 12/2004 | Zimmerling | F16K 31/088 251/7 |
| 2010/0274196 | A1 * | 10/2010 | Brandt | A61M 5/14276 604/175 |
| 2011/0054387 | A1 | 3/2011 | Stern et al. | |
| 2011/0295104 | A1 * | 12/2011 | Teitelbaum | A61B 17/068 600/409 |
| 2013/0116665 | A1 * | 5/2013 | Humayun | A61M 5/162 604/891.1 |
| 2014/0207085 | A1 | 7/2014 | Brandt et al. | |
| 2014/0228765 | A1 | 8/2014 | Burke et al. | |
| 2015/0306319 | A1 * | 10/2015 | Nessel | A61M 5/24 604/111 |
| 2016/0038672 | A1 * | 2/2016 | Brandt | A61M 5/162 604/239 |
| 2017/0043151 | A1 | 2/2017 | Bellrichard et al. | |
| 2017/0326342 | A1 * | 11/2017 | Ma | A61M 25/0612 |

OTHER PUBLICATIONS

Japan Patent Office, Office Action in related application 2021-540332, Jan. 11, 2022.

* cited by examiner

METHOD AND SYSTEM FOR PROVIDING A THERAPEUTIC AGENT TO AN IMPLANTED INFUSION DEVICE

TECHNICAL FIELD

The present disclosure relates to an implantable medical device, in particular an implantable multi-chamber infusion device, and to a method and system for refilling an implantable infusion device.

BACKGROUND

Implantable infusion devices are used to provide patients with a long term infusion of a therapeutic agent. Implantable infusion devices are e.g. used in intrathecal drug delivery systems (IDDS) to treat chronic pain. These systems deliver anesthetic agents from a reservoir through a catheter to the dorsal horn of the spinal cord.

The implantable infusion device contains a reservoir which is sealed by and accessible through a septum. The reservoir is typically refilled by injecting a hypodermic needle through a patient's skin and through the septum into the reservoir.

Implantable vascular access ports (VAP) are used in the medical field when recurrent infusions of therapeutic agents into a patient's circulatory system are required over extended periods of time. Such VAPs generally include a housing containing a reservoir and septum, with a catheter extending from the housing.

US 2004/0073196 discloses a vascular access port with a needle detector. It permits a medical professional to confirm that the needle has been correctly inserted through the septum and into the internal reservoir of the VAP. The VAP system notifies the patient and/or medical professional if the needle has been accidentally withdrawn. The content of US 2004/0073196 is hereby incorporated by reference thereto in its entirety.

US 2014/0228765 discloses a refillable and implantable infusion apparatus and method that includes a needle penetration detector that detects and indicates the position of a needle relative to a septum of a drug reservoir of the implantable infusion apparatus. With the needle position data, medical professionals may better ensure they are injecting drugs into the drug reservoir, thus, improving patient safety. The content of US 2014/0228765 is hereby incorporated by reference thereto in its entirety.

Known needle detection systems are designed to work with single-reservoir infusion devices and vascular access ports. The known systems do not address the complexity and potential failure modes of more complex multiple-reservoir infusion devices or VAPs which receive more than one therapeutic agent.

SUMMARY

An implantable infusion device includes a housing. A refill chamber is arranged within the housing. The refill chamber is accessible through a refill port. A self-sealing external septum is disposed at the refill port and forms an access opening of an upper chamber in the refill chamber. A self-sealing inner septum is disposed within the refill chamber below the external septum. The inner septum separates the upper chamber from a lower chamber. One sensor or a first sensor and a second sensor is/are arranged at the refill chamber. A processor is operatively connected to the first sensor and to the second sensor. The processor is configured, in response to signals received from the first sensor and from the second sensor, to detect a presence of a needle in the refill chamber. The processor is further configured to associate a position of a needle opening with the lower chamber or the upper chamber. Preferably, the device can not only detect the needle position, but can distinguish different types of needles.

A wireless transmitter may be operatively connected to the processor, and the processor may be configured to transmit a signal relating to the association of the position of the needle opening with the lower chamber or the upper chamber to an external device.

The first sensor may be a contact sensor arranged at a bottom of the refill chamber and the second sensor may be a Hall effect sensor or a microelectromechanical systems magnetic field sensor arranged within the housing adjacent to the refill chamber.

The first sensor and/or the second sensor may measure multiaxially. The first and/or second sensor may measure one dimensionally, two dimensionally and/or three dimensionally. This results in an improved intensity measurement of the needle. Furthermore, the detection of the direction of the needle, i.e. its vector, is improved.

An alternative single-sensor implantable infusion device may include a housing and a refill chamber arranged within the housing. The refill chamber is accessible through a refill port. A self-sealing external septum is disposed at the refill port and forms an access opening of an upper chamber in the refill chamber. A self-sealing inner septum is disposed within the refill chamber below the external septum and separates the upper chamber from a lower chamber. A magnetic field sensor is arranged at the refill chamber and operatively connected to a processor. The processor is configured, in response to a signal received from the magnetic field sensor, to detect a presence of a needle in the refill chamber and to associate, by evaluating an orientation and/or intensity of a magnetic field at the magnetic field sensor, a position of a needle opening with the lower chamber or the upper chamber.

A system for refilling an implantable infusion device includes an implantable infusing device. The implantable infusion device includes a refill chamber arranged within a housing. The refill chamber is accessible through a refill port. An upper chamber is formed within the refill chamber and accessible through a self-sealing external septum disposed at the refill port. A lower chamber is formed within the refill chamber. The lower chamber is separated from the upper chamber by a self-sealing inner septum disposed within the refill chamber. A magnetic field sensor disposed at a distance $d_{sensor}$ from a bottom of the refill chamber. A processor is operatively connected to the magnetic field sensor.

The system further includes a refill needle. The refill needle has an elongated body extending from a proximal end to a distal end. The needle includes a magnetic portion arranged at a distance $d_{magnet}$ from the distal end. A needle opening in fluid connection with the proximal end is arranged at a distance from the distal end of the elongated body. A user interface device is in wireless communication with the implantable infusion device. The distance $d_{sensor}$ is coordinated relative to $d_{magnet}$, in other words, $d_{sensor}$ and $d_{magnet}$ are adapted to each other. The magnetic field sensor and the magnet are disposed at approximately the same height, i.e. $d_{sensor}$ at least approximately equals $d_{magnet}$.

In one embodiment, $d_{sensor}$ equals $d_{magnet}$. In another embodiment, $d_{sensor}$ is slightly longer than $d_{magnet}$ so that the magnetic portion passes the sensor when it is inserted. The following proportions are beneficial: $d_{sensor}=1.0 \ldots 1.3*d_{magnet}$.

The processor is configured, in response to a signal received from the magnetic field sensor, to associate a position of the needle opening with the lower chamber or the upper chamber. The user interface device is configured to indicate the position of the needle opening in the upper chamber or the lower chamber.

The processor may be configured to recognize a correctly inserted needle if a magnetic field having a field strength above a lower threshold is detected by the magnetic field sensor. The processor may further be configured to associate a position of the needle opening with the lower chamber or the upper chamber depending on an orientation and/or intensity of a magnetic field in the magnetic portion.

A refill container filled with a therapeutic agent may be inseparably connected at the proximal end of the elongated body.

The magnetic field sensor may be a Hall Effect sensor. Alternatively, or additionally, the magnetic field sensor may be a microelectromechanical systems magnetic field sensor.

The implantable infusing device may further include a second magnetic field sensor disposed at a distance $d_{sensor2}$ from the bottom of the refill chamber. The elongated body of the refill needle may include a second magnetic portion arranged at a distance $d_{magnet2}$ from the distal end. The second sensor and the second magnetic portion may be aligned when the needle is fully inserted into the implantable infusion device, i.e. $d_{sensor2}=d_{magnet2}$. The processor may be configured to communicate information relating to an orientation and/or intensity of a first magnetic field in the magnetic portion and an orientation and/or intensity of a second magnetic field in the second magnetic portion.

A refill needle for an implantable infusion device has an elongated body extending from a proximal end to a distal end. It includes a first magnetic portion arranged at a distance $d_{magnet1}$ from the distal end, and a second magnetic portion arranged at a distance $d_{magnet2}$ from the distal end. The first magnetic portion has a selectable first magnetic field orientation and/or intensity to encode a first bit of information and the second magnetic portion has a selectable second magnetic field orientation and/or intensity to encode a second bit of information.

The first and second magnetic field may be axially oriented with magnetic poles axially spaced from one another within magnetic portion. Alternatively, the first and second magnetic field may be radially oriented with magnetic poles arranged radially inwardly and outwardly of one another. Alternatively, the first and second magnetic field may be diametrically oriented with magnetic poles of each magnetic portion arranged circumferentially opposite one another.

The elongated body may be made of molded plastic and the magnetic portion may be formed by a permanent magnet overmolded within the plastic.

The elongated body of the refill needle may include a plurality of three or more magnetic portions, each of the three or more magnetic portions being selectively magnetic in a first magnetic field orientation and/or intensity or a second magnetic field orientation and/or intensity to store one bit of information.

The elongated body may include a plurality of circumferentially spaced openings arranged at a first distance di or at a second distance $d_u$ from a distal end of the elongated body. The elongated body may include a first fluid channel which extends from a proximal end to an opening at a distance di from the distal end of the elongated body and a second fluid channel which extends from a proximal end to an opening at a distance $d_u$ from the distal end of the elongated body.

A method for refilling a multiple-reservoir infusion pump with therapeutic agents includes the following steps to fill a first reservoir: Selecting a first therapeutic agent to be filled into a first reservoir of a multiple-reservoir infusion pump. Coupling a first refill container with the first therapeutic agent with a first refill needle. The first refill needle has a first needle opening arranged at a first distance di from a distal end of the refill needle which, when the first refill needle is fully inserted into a refill port of the multiple-reservoir infusion pump, is in fluid communication with the first reservoir. Inserting the first refill needle into the refill port and delivering, e.g. delivering, the first therapeutic agent from the first refill container into the first reservoir.

The method further includes these steps to fill a second reservoir: Selecting a second therapeutic agent to be filled into a second reservoir of the multiple-reservoir infusion pump. Coupling a second refill container with the second therapeutic agent with a second refill needle. The second refill needle has a second needle opening arranged at a second distance $d_u$ from the distal end of the refill needle which, when the second refill needle is fully inserted into the refill port of the multiple-reservoir infusion pump, is in fluid communication with the second reservoir. Inserting the second refill needle into the refill port and delivering the second therapeutic agent from the second refill container into the second reservoir.

The method may further include determining, with a magnetic field sensor arranged at the refill port, the orientation and/or intensity of a magnetic field within a magnetic portion of the first refill needle and the second refill needle and distinguishing, based on the orientation and/or intensity of the magnetic field, the first refill needle from the second refill needle.

The method may also include determining, with the magnetic field sensor, presence of a magnetic field stronger than a maximum allowable threshold, and disabling the multiple-reservoir infusion pump in response to detecting the magnetic field stronger than the maximum allowable threshold.

The method may include performing an initialization measurement to determine a reference measurement value of the magnetic field sensor.

The method may further include determining, with a number of two or more magnetic field sensors axially spaced at the refill port, the orientation and/or intensity of an equal number of two or more magnetic fields within magnetic portions of the first refill needle and the second refill needle. It may then associate information retrieved from the two or more magnetic field sensors through a look-up table and communicate information retrieved from the look-up table to an external user interface device. The external user interface device may be a smartphone, a computer, or a tablet computer. The external user interface device may provide a real-time indication which of the lower and upper reservoir is being refilled.

The following detailed description of the invention is merely exemplary in nature and is not intended to limit the invention or the application and uses of the invention. Furthermore, there is no intention to be bound by any theory presented in the preceding background of the invention or the following detailed description of the invention.

DETAILED DESCRIPTION

Figure 1:
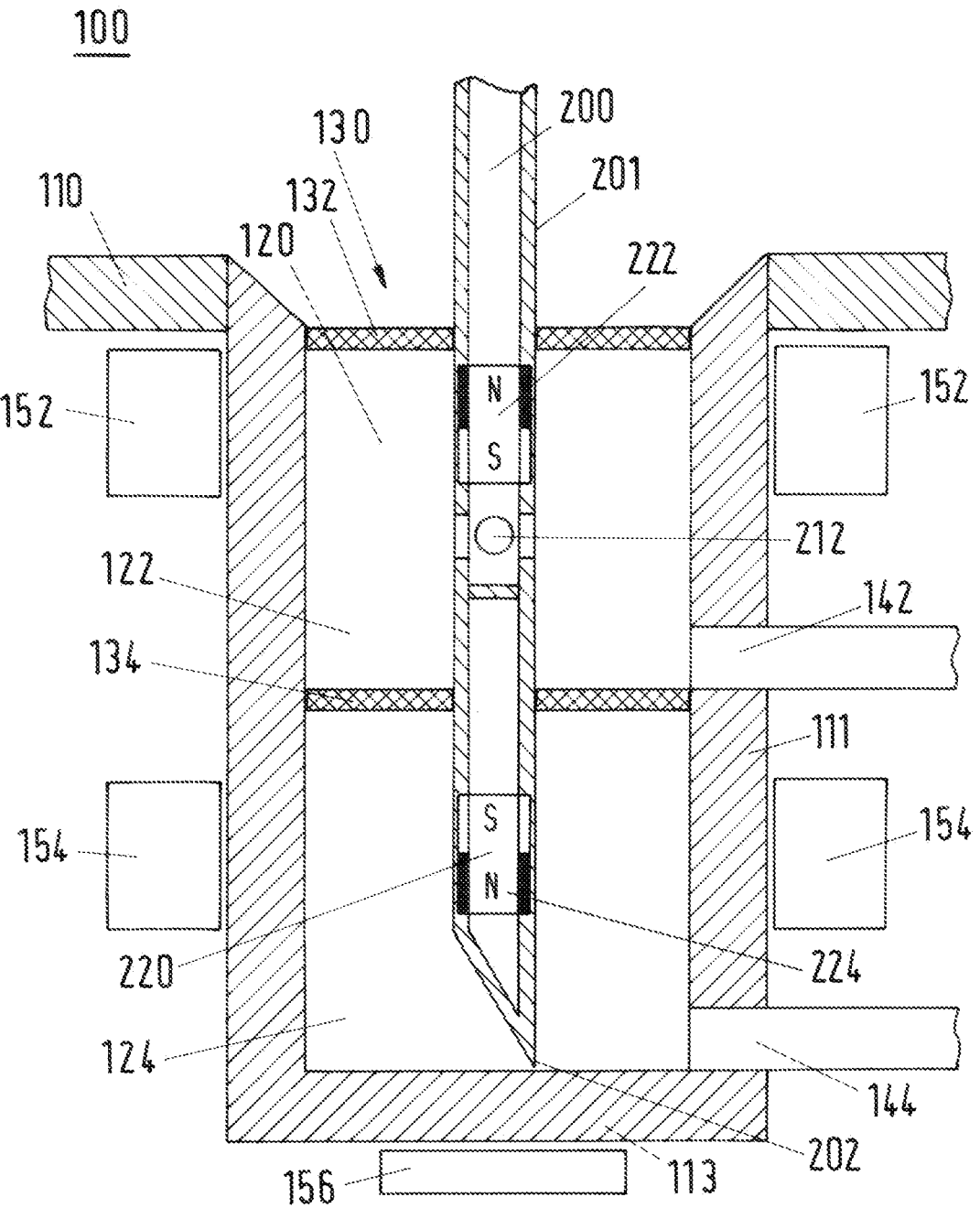
FIG. 1 shows a system for refilling an implantable infusion device.

FIG. 1 shows schematically a system for refilling an implantable multi-chamber infusion device 100 with a housing 110. The implantable infusion device 100 may be an implantable infusion pump which holds two different therapeutic agents within a refill chamber 120. The refill chamber 120 is divided into an upper chamber 122 and a lower chamber 124. The therapeutic agents may be pumped, over time, from the chambers 122, 124 through an implanted catheter into an administration area where the therapeutic agents are administered. For example, the implanted infusion device may deliver two alternative anesthetic agents from the chamber through the catheter to the dorsal horn of the spinal cord in pain management applications.

The chambers 122, 124 may be reservoirs which hold a supply of therapeutic agent. In that case, the chambers 122, 124 need to be refilled in certain time periods, for example once every month, or as needed based on a measured use of each therapeutic agent. The chambers 122, 124 may be sized to hold sufficient therapeutic agent for administration over one month, after which time they need to be refilled. Refilling the chambers 122, 124 may be performed by injecting a needle 200 through the patient's skin into a refill port 130 of the implanted infusion device 100. For that purpose, the refill port 130 includes a self-sealing external septum 132 which can be penetrated by the needle 200. The self-sealing external septum 132 reseals the chamber upon withdrawing the needle 200 from the chamber. Similarly, the upper chamber 122 and the lower chamber 124 may be separated by a self-sealing inner septum 134.

Alternatively, the chambers 122, 124 within the refill port 130 may be small and not designed to store a supply of the therapeutic agent but rather be in fluid connection with separately formed reservoirs or tanks through fluid outlets 142, 144. In an alternative configuration one of the chambers within the refill port 130 may be coupled to a tank of an implanted infusion pump while another chamber is coupled to an implanted catheter and serves as a catheter access point.

The upper and lower chamber are preferably filled with different therapeutic agents, allowing significantly more flexible therapy than single-reservoir implantable infusion pumps can provide. For example, a first therapeutic agent stored within the upper refill chamber 122 may be administered during daytime, while a second therapeutic agent stored within the lower refill chamber 124 may be administered during nighttime. Use of multi-reservoir implantable devices provides medical professionals unique treatment options, allowing different therapeutic agents to be administered based on rules programmed in the implantable infusion device.

Figures 2, 3, 4:
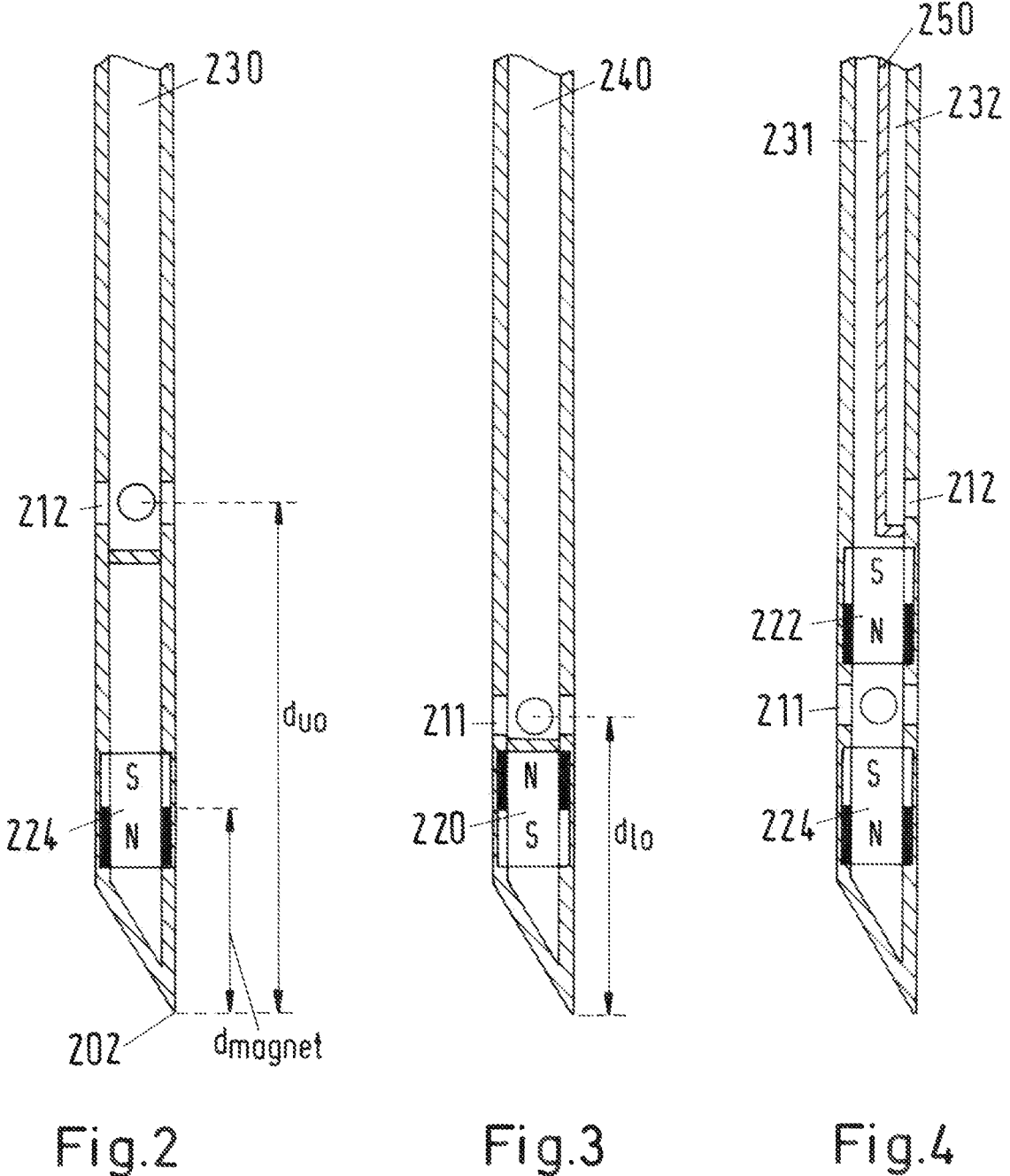
FIG. 2 shows an upper chamber refill needle.
FIG. 3 shows a lower chamber refill needle.
FIG. 4 shows a dual chamber refill needle.

The different chambers may be separately refilled by using needles 200 which are specifically configured to refill either the lower chamber 124 or the upper chamber 122. As shown in FIG. 2, an upper chamber refill needle 230 has an upper opening 212 which is positioned at an axial distance $d_{uo}$ from a tip at the distal end 202 of the needle 230. The axial distance $d_{uo}$ is selected such that the upper needle opening 212 is located in the upper chamber 122 when the needle is fully inserted into the refill chamber 120. Preferably, the distance $d_{uo}$ is selected such that the upper needle opening 212 is axially centrally located between the external septum 132 and the inner septum 134 when the needle 230 is fully inserted in the refill chamber 120.

The self-sealing external septum 132 forms an upper boundary of the upper chamber 122. The self-sealing inner septum 134 forms a lower boundary of the upper chamber 122 and an upper boundary of the lower chamber 124. The external septum 132 and the inner septum 134 may be disc-shaped and held within a cylindrical refill chamber 120. The cylindrical refill chamber 120 may extend from a bottom 113 to the refill port 130 along walls 111. The external septum 132 and the inner septum 134 may be arranged in parallel planes at an axial offset from one another.

FIG. 3 shows a lower chamber needle 240 configured to refill the lower chamber 124. A lower needle opening 211 is disposed at a distal end of the needle at a distance $d_{lo}$ from the tip. The distance $d_{lo}$ should be no longer than the distance from the bottom 113 of the refill chamber 120 to the inner septum 134. The distance $d_{lo}$ may be selected to be as short as possible.

FIG. 4 shows a dual-chamber needle 250 which can be used to simultaneous refill the upper chamber 122 and the lower chamber 124. The dual chamber needle 250 for this purpose has both a lower needle opening 211 and an upper needle opening 212. When fully inserted into the refill chamber 120, the lower needle opening 211 is located below the inner septum 134 in the lower chamber 124. The upper needle opening 212 is located above the inner septum 134 in the upper chamber 122. A first fluid channel 231 provides a fluid connection from a proximal end of the needle 250 to the lower needle opening 211. A second fluid channel 232 provides a fluid connection from the proximal end of the needle 250 to the upper needle opening 212.

While the refill chamber 120 has been shown with only one inner septum 134 and two chambers, one skilled in the art will recognize that more than one inner septum can be used to separate the refill chamber into three or more chambers. Consequently, refill needles may be configured to refill more than two chambers by having needle openings axially spaced so as to be located in between two inner septums to refill additional chambers.

One skilled in the art will also recognize that the disclosed implantable infusion device can be an implantable pump, or an implantable vascular access port which operates in combination with an external pump.

Needle detection systems for implantable infusion systems are generally known. Known systems, however, do not address the complexity and potential failure modes of multi-chamber systems. In particular, a multi-chamber system requires great diligence during refill to ensure that each chamber is filled with the correct therapeutic agent. Not only must a medical processional ensure that the right therapeutic agents are administered to the patient, but also that each of two or more therapeutic agents is filled into the correct chamber within a multi-chamber system.

A multi-chamber infusion system therefore preferably includes a needle detection and identification system. The needle detection and identification system is based on one or more sensors which are arranged at the refill chamber 120. A bottom sensor 156 may be arranged a bottom 113 of the refill chamber. The bottom sensor 156 may be a contact sensor, such as a pressure-sensitive switch, to detect that a needle 200 has been fully inserted into the refill chamber 120. In this configuration, the bottom sensor 156 serves only to detect a presence of, but not to identify the needle 200.

Alternatively, the bottom sensor 156 may be a magnetic field sensor configured to detect a magnetic field associated with a magnetic portion 220 of the needle. That is, the needle 200 may include within its elongated body 201 a magnetic portion 220. The magnetic portion 220 may be formed by a permanent magnet which is embedded within the body 201 of the needle 200. The permanent magnet may be an axially magnetized permanent ring magnet which has been over-molded within a needle body 201 made of plastic. In a basic implementation of a needle detection and identification system a single magnetic portion 220 may interact with a bottom magnetic field sensor 156. The magnetic field sensor 156 may be operatively connected to a microprocessor which is configured to read and evaluate signals from the magnetic field sensor 156. The microprocessor may thereby detect presence of the needle 200 within the refill chamber 120 when the strength of a magnetic field at the sensor 156 exceeds a threshold. The threshold may be a predetermined fixed value, or may depend on a magnetic field strength measurement performed before the needle 200 is inserted.

The magnetic field sensor 156 may further be used to identify and distinguish the needle 200 as being lower chamber needle 240 or an upper chamber needle 230. For this purpose, the upper chamber needle 230 may have a lower magnetic portion 224 in which the magnetic field is polarized opposite to the magnetic field of a corresponding lower chamber needle 240. As shown in FIG. 2, the upper chamber needle 230 has a magnetic portion 224 with a magnetic north pole arranged towards the distal end of the needle. The corresponding lower chamber needle 240 shown in FIG. 3 has a magnetic portion 220 arranged at the same distance from the tip of the needle, but with opposite polarity. The magnetic south pole of the lower chamber needle 240 is at the same distance from the distal end of the needle as the magnetic north pole of the upper chamber needle 230.

A processor (not shown) which is in communication with the bottom magnetic field sensor 156 can determine whether a needle is fully inserted by checking for a presence of a magnetic field of sufficient strength irrespective of the polarization of the magnetic field. The same bottom sensor 156 can be used to identify a needle as a lower or upper chamber needle by determining the polarization of the magnetic field in the needle.

As shown in FIG. 1, more than one sensor can be used. For example, an upper magnetic field sensor 152 and a lower magnetic field sensor 154 may be arranged at the refill chamber 120. The upper magnetic field sensor 152 and the lower magnetic field sensor 154 may include Hall Effect sensor elements or microelectromechanical systems magnetic field sensor elements. Each magnetic field sensor may include more than one Hall Effect sensor element or micro-electromechanical systems magnetic field sensor elements, and may e.g. include two or three Hall Effect sensor elements or microelectromechanical systems magnetic field sensor elements circumferentially distributed around the refill chamber at the same or varying axial distance from the bottom 113 of the refill chamber.

A microelectromechanical systems (MEMS) magnetic field sensor is a small-scale device. It can detect and measure magnetic fields. Such a sensor may detect effects of the Lorentz force, e.g. it may electronically measure a change in voltage or resonant frequency, or it may optically measure a mechanical displacement. Temperature effects should be compensated for. MEMS magnetic field sensor comprise a variety of parameters, e.g. a resonance frequency, a mode shape, a responsivity, a quality factor, or a resolution.

The resonance frequency is the frequency with the highest or longest vibration amplitude of the MEMS magnetic field sensor. The pattern of the vibration of the sensor is the mode shape. The size of the oscillation being achieved with the same external condition is described by the responsivity. The quality factor describes how much energy is maintained by the resonator during the vibration. The resolution describes the smallest measurable magnetic field.

MEMS magnetic sensors are very small and may detect very small magnetic fields. Thus, a magnetic field measurement by a MEMS magnetic field sensor has a high resolution. Furthermore, the MEMS magnetic field sensor may be placed close to the source of the magnetic field, i. e. close to the position refill needle.

A magnetic field sensor may consist of one or more sensing elements configured to detect the strength and/or orientation of the magnetic field.

Use of magnetic field sensors 152, 154 and use of multiple sensor elements per magnetic field sensors allows complex processing of sensor signals to triangulate and thereby more accurately determine the position of the needle within the refill chamber.

Furthermore, the implantable device may comprise more than two magnetic field sensors. For example, a third magnetic field sensor may determine magnetic field of the surrounding of the implant and refill port. That third magnetic field sensor may be arranged in the housing of the implantable infusion device.

A refill needle may include two or more magnetic portions axially spaced from one another. Preferably, the axial position of the magnetic portions in the needle corresponds to the axial position of magnetic field sensors at the refill chamber. As shown in FIG. 1, the upper magnetic portion 222 of the needle 200 is approximately axially aligned, when the needle is fully inserted, with the upper magnetic field sensor 152. The lower magnetic portion 224 is axially aligned with the lower magnetic field sensor 154 when the needle 200 is fully inserted.

Figures 5, 6, 7:
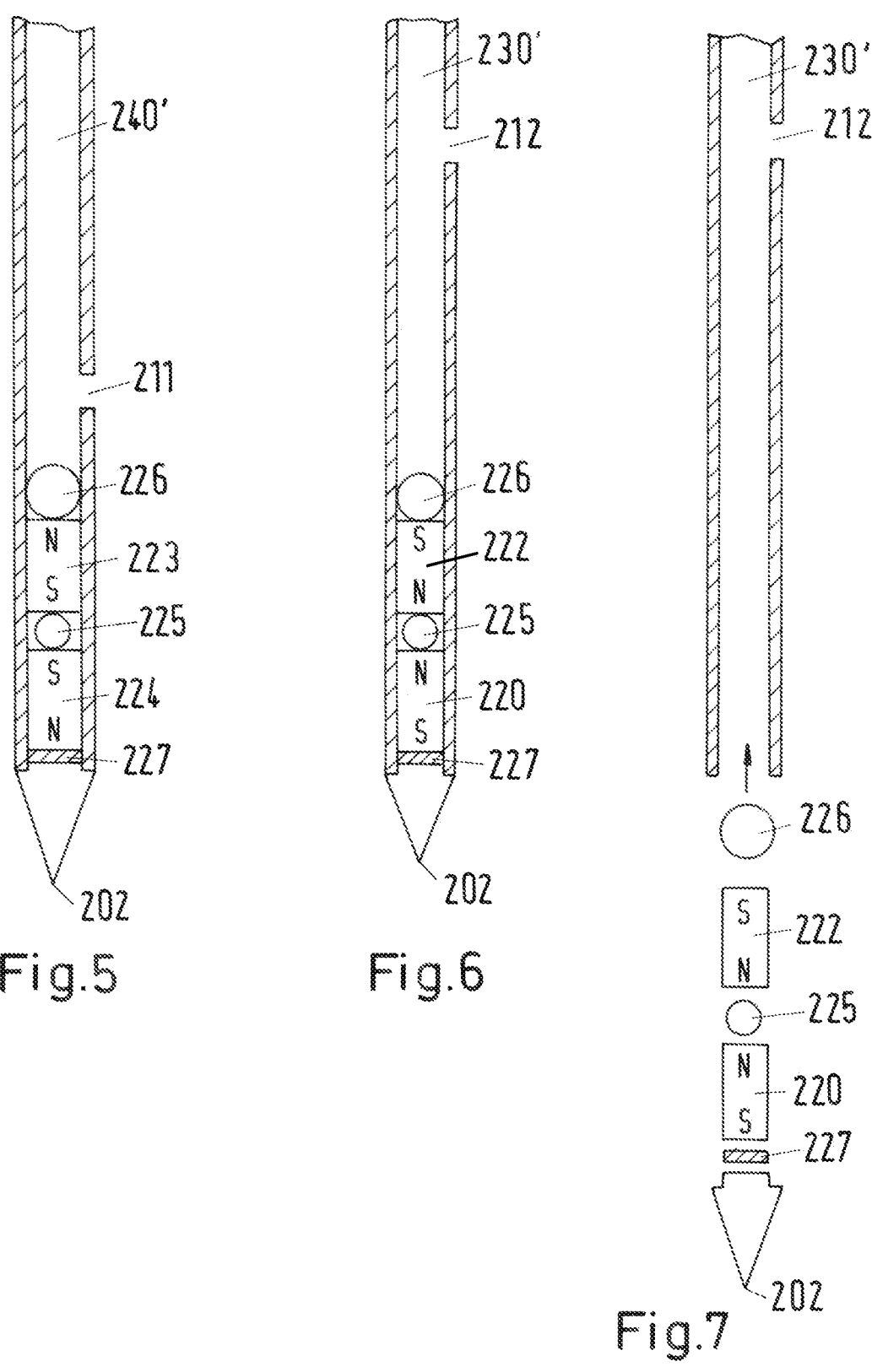
FIG. 5 shows another lower chamber refill needle.
FIG. 6 shows another upper chamber refill needle.
FIG. 7 shows an exploded view of FIG. 6

Preferably, as shown in FIG. 5, a further lower chamber refill needle 240' is shown. In that example, the lower chamber refill needle 240' may include a lower magnetic portion 224 and an upper magnetic portion 223. A distance element 225, which may be a ball, may space apart the lower magnetic portion 224 from the upper magnetic portion 223.

A sealing element 226 may separate at least one lower needle opening 211 from the lower magnetic portion 224 and the upper magnetic portion 223. Thus, the lower needle opening 211 is arranged proximal to the lower magnetic portion 224 and upper magnetic portion 223.

The magnetic field of the lower magnetic portion 224 is polarized opposite to the magnetic field of the upper magnetic portion 222. In that example, the lower magnetic portion 224 comprises a south pole on the proximal end and a north pole on the distal end. The upper magnetic portion 222 comprises a north pole on the proximal end and a south pole on the distal end.

A cap 227 is arranged distal to the lower magnetic portion 224. The cap 227 and the sealing element 226 hold the lower magnetic portion 224 and the upper magnetic portion 222 in place.

The distal end 202 of the refill needle 240' may comprise a central tip. The central tip may comprise three sharpened sides.

FIG. 6 shows another upper chamber refill needle 230'. In that example, the upper chamber refill needle 230' may include a lower magnetic portion 220 and an upper magnetic portion 222. A distance element 225, which may be a ball, may space apart the lower magnetic portion 220 from the upper magnetic portion 222.

A sealing element 226 may separate at least one upper needle opening 212 from the lower magnetic portion 220 and the upper magnetic portion 222. Thus, the upper needle opening 212 is arranged proximal to the lower magnetic portion 220 and upper magnetic portion 222. Furthermore, the position of upper needle opening 212 is closer to the proximal end of the upper chamber refill needle 230' than the position of the lower needle opening 211 of the lower chamber refill needle 240'.

The magnetic field of the lower magnetic portion 220 is polarized opposite to the magnetic field of the upper magnetic portion 222. Furthermore, the polarization is opposite to the example of FIG. 5. In FIG. 6, the lower magnetic portion 220 comprises a north pole on the proximal end and a south pole on the distal end. The upper magnetic portion 222 comprises a south pole on the proximal end and a north pole on the distal end. The polarization of the magnetic portions of the example shown in FIG. 6 is therefore opposite to the polarization of the magnetic portions of the example shown in FIG. 5.

A cap 227 is arranged distal to the lower magnetic portion 220. The cap 227 and the sealing element 226 hold the lower magnetic portion 220 and the upper magnetic portion 222 in place.

The distal end 202 of the refill needle 230' may comprise a central tip. The central tip may comprise three sharpened sides.

FIG. 7 shows an explosion view of the upper chamber refill needle 230' of FIG. 6. For manufacturing the refill needle, the sealing element 226, the upper magnetic portion 222, the distance element 225, and the lower magnetic portion 220 are pressed into the distal opening of a cannula of the refill needle 230'. The sealing element 226, the upper magnetic portion 222, the distance element 225, and the lower magnetic portion 220 may comprise a diameter being slightly bigger than the diameter of the cannula. In that case, pressing the sealing element 226, the upper magnetic portion 222, the distance element 225, and the lower magnetic portion 224 into the cannula fixes their position in the refill needle.

The cap 227 may be pressed into the distal opening of the cannula to fix the input in the cannula. However, the cap 227 may also be fixed in the cannula by another method.

Then, the central tip is pressed into the distal opening at the distal end 202 of the refill needle. Alternatively, the central tip may be glued or welded into the distal opening at the distal end.

The manufacturing mentioned above also applies to the lower chamber refill needle 240'.

The configuration of the magnetic portions 220, 222 of the examples in FIGS. 5 and 6 results in a magnetic field at the distance element 225 that is turned by 90° with respect to the sensor. This means, when inserting the refill needle into the infusion device the orientation of the magnetic field lines will turn from a direction parallel to the axis of the refill needle to a direction orthogonal to the axis of the refill needle. This allows the sensor to detect the position of magnetic field which is in close alignment to the distance element 225 with high accuracy.

The refill needle may comprise an outer diameter in the range from 0.4 mm to 1.0 mm, preferably of 0.7 mm. An inner diameter of the refill needle may be in the range from 0.2 mm to 0.8 mm, preferably 0.5 mm.

A diameter of the needle opening may be in the range from 0.1 mm to 0.7 mm, preferably 0.35 mm. The distance of the center of the needle opening from the central tip may be in the range of at least 6.0 mm to 80.0 mm.

A diameter of the distance element 225, the upper magnetic portion 222, and the lower magnetic portion 224 may be in the range between 0.2 mm to 0.6 mm, preferably 0.4 mm. A distance of the distance element 225 from the central tip may be between 2.0 mm and 3.7 mm, preferable 3.15 mm.

Figure 8:
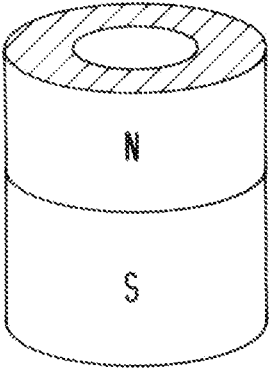
FIG. 8 shows a magnetic portion with axial orientation.
Figure 9:
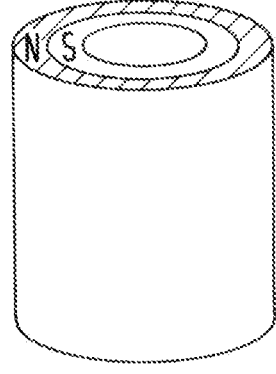
FIG. 9 shows a magnetic portion with radial orientation.
Figure 10:
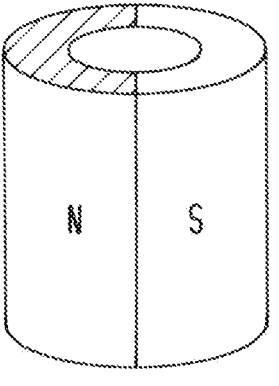
FIG. 10 shows a magnetic portion with diametic orientation.
Figure 11:
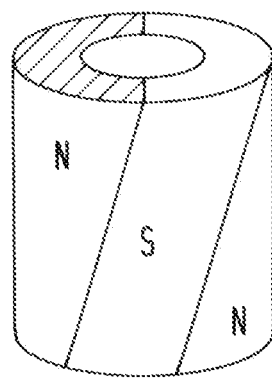
FIG. 11 shows a magnetic portion with skewed orientation.

Various magnetic field configurations can be employed for the magnetic portion 220. For example, as shown in FIG. 8, the magnetic field can be axially oriented with magnetic poles axially spaced from one another within magnetic portion. Alternatively, as shown in FIG. 9, the magnetic field can be oriented radially with magnetic poles arranged radially inwardly and outwardly of one another. As shown in FIG. 10, the magnetic field can be diametrically oriented with magnetic poles of each magnetic portion arranged circumferentially opposite one another. As shown in FIG. 11 the magnetic field can be skewed.

While FIGS. 9 and 10 show two-pole configurations of the straight and skewed magnetization, multi-pole configurations can also be used.

Furthermore, FIGS. 8 to 11 show magnetic portions comprising bores in axial direction. However, those bores are optional. Thus, the magnetic portions as shown in FIGS. 8 to 11 may be free from bores.

Use of two or more magnetic portions 220, 222 within a needle allows encoding two or more bits of information. For example, when using axial magnetic field orientations one bit of information can be encoded by choosing a "distal north" or "distal south" configuration. Similarly, one bit of information can be encoded in a radial magnetic field orientation by choosing a "outside north" or "outside south" configuration. The relative circumferential orientation of diametrically oriented magnetic fields can be used to encode one or more bits of information. Absence of a magnetic field can be used to encode information. Information magnetically encoded within the needle may be used to identify the needle, for example to recognize a needle as an upper or lower chamber needle.

Additional information may be magnetically encoded within the needle and associated with a look-up table stored within a processor in the infusion device or an external device which is in wireless communication with the infusion device. The additional information may be used to eliminate further potential failure modes. For example, the needle may be firmly and inseparably attached to a refill reservoir which is prefilled with a therapeutic agent. In that case, the needle can be encoded to identify the therapeutic agent. The infusion device may, through its two or more magnetic field sensors, read information magnetically encoded within the needle and communicate the information to an external device. A processor within the infusion device may be programmed to provide an alert if an incorrect needle is inserted into its refill chamber. For example, the infusion device may be programmed to recognized that is should be filled with a therapeutic agent A in the lower refill chamber 124 and a therapeutic agent B in the upper chamber 122. If a needle encoded to be associated with a therapeutic agent C is inserted into the refill chamber 120 an alert is issued. Similarly, an alert is issued if an upper chamber needle 230 encoded to contain therapeutic agent A is inserted, alerting a medical processional to the incorrect association of agent and chamber.

The infusion device may include a feedback actuator, e.g. a vibration element, to communicate the correct or incorrect insertion of a needle directly to a patient, e.g. through haptic feedback.

During refill, a lower magnetic portion 224 of the needle 200 may interact with an upper magnetic field sensor 152 which is arranged near the external septum 132. In particular, two or more Hall Effect sensors or microelectromechanical systems magnetic field sensors 152 arranged at the refill port 130 can be used to triangulate a position of the needle 200, ideally even before piercing a patient's skin to properly position the needle centrally within the refill port 130. For this purpose, the processor may evaluate a field strength of a magnetic field at two or more Hall Effect sensors or microelectromechanical systems magnetic field sensor elements and provide, through an external user interface device, positioning instructions to achieve equal field strengths at all sensors. For that purpose the implantable infusion device may include a wireless transmitter operatively connected to the processor.

The upper magnetic field sensor 152 and the lower magnetic field sensor 154 need not be sensitive in the same plane. For example, the upper magnetic field sensor 152 can be configured to sense a radially oriented magnetic field in an upper magnetic portion 222 of the needle 200. The lower magnetic field sensor 154 may at the same time be configured to sense an axially oriented magnetic field of the lower magnetic portion 220. Of course, magnetic field sensors can be configured to sense multiple different magnetic field orientation and/or intensities, so that the type of magnetic field (axial, radial, multi-pole, etc.) can be used to encode further information within the needle 200.

It can be beneficial to maximize the information derived from each magnetic field sensor 152, 154 by evaluating its sensors output over time and thus analyzing a change in the magnetic field around the sensor as an encoded needed is inserted into the refill port 130. A processor connected to the magnetic field sensors 152, 154 may e.g. sample a sensor output multiple times per second to determine a maximum field strength of the magnetic field around the sensor, or a length of a magnetic portion of the needle. A number of $n \geq 1$ magnetic field sensors may be used to analyze a greater number of $m \geq 1$ magnetic portions of a needle.

One or more magnetic field sensors of the infusion device can be used to detect presence of a strong magnetic field indicative of the device being within a MRI device. The processor may be configured to, upon detecting an excessive magnetic field, shut down pumps and/or close valves within the device to prevent incorrect dosage of therapeutic agents while the device is exposed to the magnetic field of an MRI device.

Figure 12:
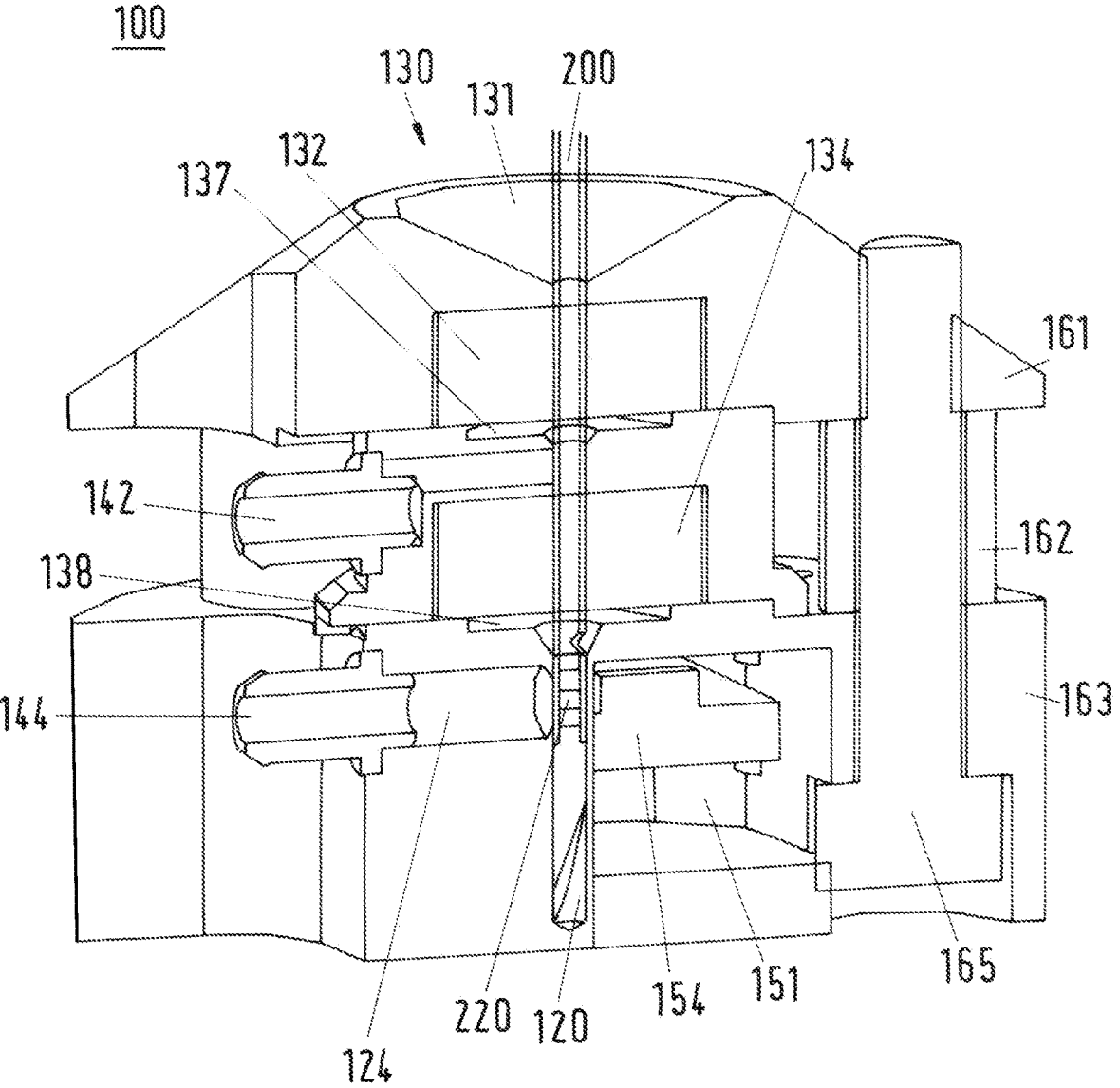
FIG. 12 is a perspective cross sectional rendering of a system for refilling an implantable infusion device.
Figure 13:
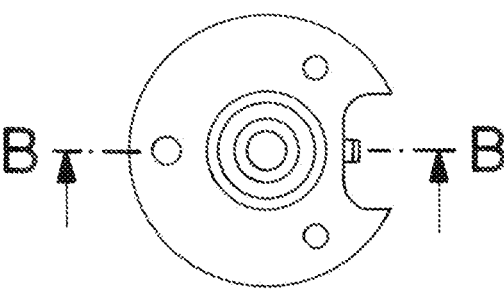
FIG. 13 is a top view of a system for refilling an implantable infusion device.
Figure 14:
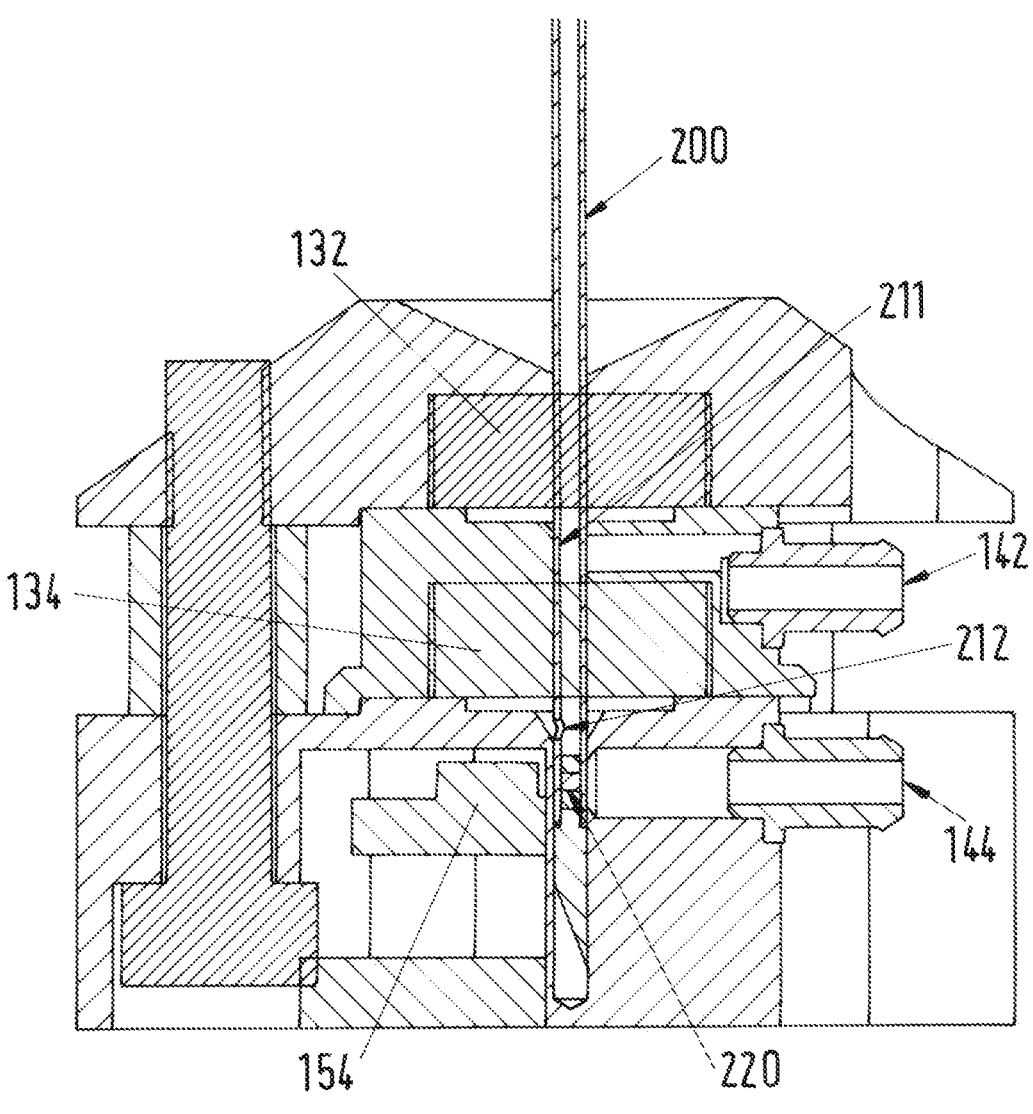
FIG. 14 is a cross sectional view B-B of FIG. 13.

Referring now to FIGS. 12-14, different views of a port for an implantable infusion device 100 are shown. The implantable infusion device 100 may combine aspects of an implantable infusion pump with aspects of a catheter access port (CAP) with a single port 130. The infusion device 100 here includes a relatively narrow generally cylindrical port chamber 120. As shown, the diameter of the port chamber 120 is only slightly larger than the diameter of the refill needle 200. The diameter of the port chamber 120 may be less than two times the diameter of the refill needle, less than 1.5 times the diameter of the refill needle, or even less than 1.2 times the diameter of the refill needle.

To introduce the needle in the port chamber 120 an external port guide 131 is provided. The external port guide 131 has a frustoconical shape which terminates into a cylindrical opening. The external port guide 131 is generally shaped and functional like a funnel. An outer diameter of the external port guide 131 may be more than 10 times, more than 20 times, or even more than 30 times greater than the diameter of the needle 200. The external septum 132 is arranged at the lower, inner end of the external port guide 131.

The external septum 132 may be a disk-shaped mass of silicone held within a widened portion of the port chamber 120 between an upper wall and a lower wall. The upper wall may be the part of the external port guide 131. An external septum cavity 137 may be formed below the external septum 132 with a diameter smaller than the diameter of the external septum 132, yet significantly larger than the diameter of the needle 200.

Fluid outlets 142, 144 are arranged perpendicularly to a longitudinal axis of the port chamber 120. A first fluid outlet, e.g. the lower fluid outlet 144, may be directly coupled to an implanted catheter. In respect to the lower fluid outlet the implanted infusion device 100 thus acts as a catheter access port, e.g. a vascular access port, which can be used to administer a therapeutic agent while the needle 200 is inserted into the port and externally supplied with the therapeutic agent.

A second fluid outlet, e.g. the upper fluid outlet 142, may be in fluid communication with a refillable tank of an implanted infusion pump. The tank may be formed as a bellows which expands and contracts with an amount of therapeutic agent therein.

One or more magnetic portions 220 of the refill needle may be arranged towards the distal end of the needle 200 below the lowest fluid opening. In this case, the magnetic portion 220 can be formed by a solid cylindrical magnet which is inserted into a hollow space within the needle 200. One or more magnetic field sensors 154 may be arranged proximal to the bottom of the port chamber below the lower chamber, spaced from the bottom so as to approximately align with the magnetic portion 220 of the needle 200. Two or more magnetic field sensors (not shown) can be stacked along the axial extension of the needle within a sensor chamber 151 at a lower end of the refill port 130.

The refill port 130 may be made of separately machined portions 161, 162, 163 which are stacked on top of one another and held together by screws 165. As shown, the external septum 132 may be held within an upper portion 161 of the port 130. The inner septum 134 and the upper fluid outlet 142 may be arranged within a center portion 162 of the refill port. The lower fluid outlet 144 may be arranged within a lower portion 163 of the port 130. Septum cavities 137, 138 may be formed at upper ends of the center portion 162 and lower portion 163 to hold the respective septum within the portion above, and provide a space for the septum to expand into when the needle 200 is inserted into the septum.

Throughout this specification and the following claims the indefinite article "a" or "an" means "one or more". Reference to "a first element" does not mandate presence of a second element.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations and broad equivalent arrangements that are included within the spirit and scope of the following claims.

What is claimed is:

1. A set of refill needles for an implantable infusion device, comprising:

a lower chamber needle configured to refill a lower chamber of the implantable infusion device; and an upper chamber needle configured to refill an upper chamber of the implantable infusion device, the lower chamber needle and the upper chamber needle each having an elongated body extending from a proximal end to a distal end including a first magnetic portion arranged at a distance ($d_{magnet1}$) from the distal end, wherein the first magnetic portion of the lower chamber needle has a first magnetic field orientation and the first magnetic portion of the upper chamber needle has a second magnetic field orientation different from the first magnetic field orientation, and/or wherein the first magnetic portion of the lower chamber needle has a first magnetic field intensity and the first magnetic portion of the upper chamber needle has a second magnetic field intensity different from the first magnetic field intensity to encode a first bit of information, and wherein the lower chamber needle has a lower needle opening positioned at a first axial distance from the distal end of the lower chamber needle, and wherein the upper chamber needle has an upper needle opening positioned at a second axial distance from the distal end of the upper chamber needle, the second axial distance being greater than the first axial distance, and wherein the first magnetic field orientation or the first magnetic field intensity identifies a refill needle from the set of refill needles as the lower chamber needle, and wherein the second magnetic field orientation or the second magnetic field intensity identifies a refill needle from the set of refill needles as the upper chamber needle.

2. The set of refill needles as in claim 1, wherein a first magnetic field of the first magnetic portion is axially oriented.

3. The set of refill needles as in claim 1, wherein the first magnetic field is radially oriented with magnetic poles arranged radially inwardly and outwardly of one another.

4. The set of refill needles as in claim 1, wherein the first magnetic field is diametrically oriented with magnetic poles arranged circumferentially opposite one another.

5. The set of refill needles as in claim 1, wherein each elongated body is made of molded plastic and wherein the first magnetic portion is formed by a permanent magnet overmolded within the plastic.

6. The set of refill needles as in claim 1, wherein each elongated body includes a plurality of two or more magnetic portions, each of the two or more magnetic portions being selectively magnetic in a first magnetic field orientation or a second magnetic field orientation to store one bit of information.

\* \* \* \* \*